United States Patent [19]

Bristol et al.

[11] 4,361,567
[45] Nov. 30, 1982

[54] TREATMENT OF PEPTIC ULCER DISEASE

[75] Inventors: James A. Bristol, Ann Arbor, Mich.; Raymond G. Lovey, West Caldwell, N.J.

[73] Assignee: Schering Corporation, Kenilworth, N.J.

[21] Appl. No.: 308,348

[22] Filed: Oct. 5, 1981

[51] Int. Cl.³ .................... A61K 31/44; C07D 487/04
[52] U.S. Cl. .................................... 424/256; 546/121
[58] Field of Search ......................... 546/121; 424/256

[56] References Cited

U.S. PATENT DOCUMENTS 3,790,586  2/1974  Irikura et al. ...................... 546/121

FOREIGN PATENT DOCUMENTS 47-30693  9/1972  Japan .................................. 546/121

OTHER PUBLICATIONS

J. D. Bower et al, Chem. Soc. Jour., (London), (1955), pp. 2834–2837.

Primary Examiner—Norma S. Milestone
Attorney, Agent, or Firm—Gerald S. Rosen; Bruce M. Eisen

[57] ABSTRACT

Disclosed herein are certain imidazo[1,5-a]pyridines, and pharmaceutical compositions containing them as the active ingredient for treatment and promotion of healing of peptic ulcer disease by virtue of their antisecretory and cytoprotective properties.

10 Claims, No Drawings

TREATMENT OF PEPTIC ULCER DISEASE

SUMMARY OF THE INVENTION

This invention relates to therapeutic compositions and to their use in the treatment and promotion of healing of peptic ulcer disease with certain imidazo[1,5-a]pyridines substituted on the imidazo ring at the one and/or three positions with methyl and/or cyanomethyl.

BACKGROUND OF THE INVENTION

Peptic ulcer disease is manifested by ulceration of the mucous membrane of the esophagus, stomach and/or duodenum. The etiology of peptic ulcer disease remains uncertain. However, it is known that hydrochloric acid secreted by the parietal cells of the stomach is intimately involved in the disease process.

Many attempts have been made to develop drugs which inhibit gastric acid secretion or neutralize gastric contents and thus provide therapeutic utility in the treatment of peptic ulcer disease. To date, compounds which have been shown to be effective in reducing symptoms of peptic ulcer disease are those which reduce gastric acid secretion via H-2 receptor antagonism and those which, when taken in adequate amounts, are therapeutically equivalent to H-2 receptor antagonists.

In recent years, the accepted treatment for peptic ulcer disease has depended upon drugs such as antacids which neutralize gastric acid, anticholinergics and H-2 receptor antagonists which reduce acid secretion in the stomach, and drugs such as sucralfate and carbenoxolone which increase the rate of healing of peptic ulcers but do not inhibit gastric acid secretion. These latter compounds may have cytoprotective (mucoprotective) activities similar to the prostaglandins and prostaglandin analogs.

A search has been underway for a compound which has both antisecretory and cytoprotective effects. Such a combination of effects would be expected to have therapeutic utility in treatment of peptic ulcer disease and possibly other diseases of the upper gastrointestinal tract such as "stress ulcer", erosive gastritis and esophogitis; and treatment of pathological hypersecretory conditions such as Zollinger-Ellison syndrome, systemic mastocytosis and multiple endocrine adenomas, as well as limiting gastrointestinal damage associated with the use of other drugs.

In recent years, efforts to utilize imidazo[1,5-a]-pyridines to treat peptic ulcer disease and provide cytoprotective effects have not been entirely successful since such compounds have been found to exhibit only antisecretory effects.

Thus, Durant et al., in U.S. Pat. No. 4,024,271 and No. 4,228,291, disclose that certain 5,6,7,8-tetrahydroimidazo-[1,5-a]pyridines are useful in inhibiting histamine H-2 receptors and certain actions of gastrin at daily dosages of from about 150 mg. to about 1000 mg. There is no disclosure of cytoprotective activity.

Irikma et al., U.S. Pat. No. 3,790,586, disclose 3-aminoimidazo[1,5-a]pyridines with optional substituents at the 1, 5 and 7 positions which exhibit excellent gastric antisecretory action. There is no disclosure of cytoprotective activity.

Kyorin Pharmaceutical Co. Ltd., Japan 4730693-Q Sept. 11, 1972, discloses 3-acylaminoimidazo[1,5-a]pyridines, optionally substituted in the 1, 5 and 7 positions, which inhibit gastric acid secretion. There is no disclosure of cytoprotective activity.

DETAILED DESCRIPTION OF THE INVENTION

This invention provides compositions for treating and promoting the healing of peptic ulcer disease containing, as the active antisecretory and cytoprotective compound, a compound represented by the formula

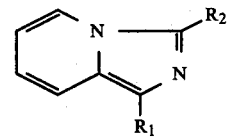

wherein $R_1$ represents hydrogen or cyanomethyl; and $R_2$ represents methyl or cyanomethyl; and pharmaceutically acceptable salts thereof.

As used herein, "pharmaceutically acceptable salts" includes pharmaceutically acceptable acid addition salts which salts of the active compounds prepared by reaction with organic and inorganic acids such as hydrochloric, sulfuric, phosphoric, nitric, acetic, propionic, maleic, ascorbic, citric and the like and quaternary salts which are quaternary ammonium salts of the active compounds prepared by reaction with e.g., organic halides such as methyl iodide, benzyl bromide and the like.

The active compounds of this invention can be prepared from an appropriately substituted 2-aminomethylpyridine as described in Bower et al., J. Chem. Soc. 2834 (1955). The active compounds of this invention are, in part, novel, i.e. those in which at least one of $R_1$ and $R_2$ are cyanomethyl, are novel compounds.

The desired criteria for chemical compounds used to promote healing of gastric and/or duodenal ulcers as well as to relieve the symptoms of peptic ulcer disease and of "stress ulcer", erosive gastritis and esophogitis and to treat pathological hypersecretory conditions of the upper gastrointestinal tract and limit or prevent damage to the gastrointestinal tract associated with the use of other drugs, are that the compounds have gastric antisecretory effects and/or cytoprotective activity and cause minimal undesired side effects. Other desirable criteria are that the compounds have a rapid onset of action, require a small effective dose, display a satisfactory duration of action and display continued identical responses to subsequently repeated doses. It is also desirable that such compounds be amenable to oral and parenteral administration.

The active compounds of this invention fulfill the desired criteria and are thus useful for the treatment of peptic ulcer disease and for promoting the healing of gastric and/or duodenal ulcers by virtue of their antisecretory and/or cytoprotective activities. The compounds are also useful as conjunctive therapeutic agents for coadministration with drugs which tend to irritate or ulcerate the upper gastrointestinal tract, e.g. anti-inflammatory/analgesic agents such as aspirin, indomethacin, phenylbutazones, ibuprofen, naproxen, tolmetin and the like.

For use as gastric antisecretory agents and cytoprotective agents (also referred to as mucoprotective agents), the active agents are formulated, using conventional inert pharmaceutical adjuvant materials, into dosage forms which are suitable for oral, parenteral or suppository administration. Such dosage forms include tablets, suspensions, solutions, hard or soft capsules, dragees and the like. The identity of the inert adjuvant materials which are used in formulating the active compounds into oral and parenteral dosage forms as well as suppositories will be immediately apparent to persons skilled in the art. These adjuvant materials, either organic or inorganic in nature, include, for examples, water, gelatin, albumin, lactose, starch, magnesium stearate, preservatives, stabilizers, wetting agents, emulsifying agents, salts for altering osmotic pressure, buffers, etc., which can be incorporated, if desired, into such formulations.

The quantity of active agent which is present in any of the above described dosage forms generally varies from about 20 to 530 mg.

The active compounds of this invention are effective for oral treatment of the ulcerative disease states mentioned herein at doses of about 0.5 to 50 mg./kg. of body weight per day, preferably being administered in 2–4 divided doses per day. In those instances wherein it is desired to administer the active compounds parenterally, e.g. intravenously, they are administered at a dosage range of about 0.01 to 10 mg./kg. of body weight in single or multiple daily doses. Of course, the dosage administration to a particular patient is variable and will depend on the clinicians judgment using as the criteria the age, condition and size of the patient, the potency of the active compound and the patient's response thereto. An effective dosage amount of active agent can therefore only be determined by the clinician utilizing his or her best judgement on the patient's behalf. The recommended dosage for the compounds of this invention is an oral dose of 75 to 1600 mg/day, preferably 600–800 mg/day, in two to four divided doses to achieve relief of the symptoms of peptic ulcer disease and promote the healing of gastric and/or duodenal ulcers.

The antisecretory effects and/or cytoprotective properties of the active compounds of this invention are manifested in standard biological procedures in which the active compounds are evaluated both on an absolute basis and on a comparative basis with compounds known to have either antisecretory effects sufficient to treat and/or prevent peptic ulcer disease and drug induced ulceration, and compounds known to have useful cytoprotective effects.

In a test for antisecretory effects using the pyloric ligation technique the compounds are administered in appropriate and well-defined and well-known vehicles by either intraperitoneal or oral administration to rats.

In a test for cytoprotective effects, the test compound is administered orally to rats prior to oral delivery of absolute ethanol.

Positive results in both the mentioned tests indicate the compounds of this invention have both antisecretory and cytoprotective activity.

The following examples illustrate the preparation of the active compounds and pharmaceutical formulations containing the active compounds. All temperatures are in degrees Celsius.

EXAMPLE 1

Add dropwise with stirring a freshly prepared solution of 20.6 gm (0.2 mol) cyanoacetyl chloride in 40 ml tetrahydrofuran (THF) to a cooled solution of 21.5 gm (0.2 mol) 2-aminomethylpyridine and 28 ml triethylamine in 500 ml THF in a reaction flask. Stir the reaction mixture at room temperature for one hour, and filter off triethylamine hydrochloride which is formed. Concentrate the resulting filtrate under reduced pressure and chromatograph the resulting residue on silica gel using ethyl acetate-dichloromethane.

Combine the fractions containing 2-cyano-N-(2-pyridylmethyl)acetamide, as determined by IR and NMR, NMR, and remove the solvent under reduced pressure. Triturate the residue in ether and recrystallize from ethyl acetate to obtain 2-cyano-N-(2-pyridylmethyl)acetamide, m.p. 82°–83°.

EXAMPLE 2

Heat under reflux for 0.5 hours a mixture of 9 gm (0.06 mol) 2-cyano-N-(2-pyridylmethyl)acetamide and 100 ml phosphorous oxychloride. Cool the reaction mixture to room temperature and remove the phosphorus oxychloride under reduced pressure. Partition the residue between chloroform and a solution of sodium bicarbonate. Separate the chloroform layer and dry over anhydrous potassium carbonate. Filter and remove the chloroform under reduced pressure. Chromatograph the resulting residue on silica gel using ethyl acetate-chloroform to give the desired product, 3-cyanomethyl imidazo[1,5-a]pyridine, as determined by IR, NMR and elemental analysis, m.p. 64°–66°.

EXAMPLE 3

Heat under reflux for 2 hours a mixture containing 5.5 gm (0.042 mol) 3-methylimidazo[1,5-a]pyridine [Bower et al., J. Chem. Soc. 2834 (1966)], 3.6 gm (0.044 mol) dimethylamine hydrochloride and 1.56 gm (0.052 mol) paraformaldehyde in 75 ml ethanol. Cool to room temperature and remove the ethanol under reduced pressure. Partition the resulting residue between chloroform and 10% aqueous sodium hydroxide. Extract the basic aqueous layer with chloroform and combine the chloroform extracts. Remove the water from the chloroform extracts over anhydrous sodium sulfate. Filter the resulting dried chloroform extracts, and remove the chloroform under reduced pressure. Dissolve the resulting residue in 150 ml acetone, add 2.2 ml (0.035 mol) methyl iodide to the solution, and stir at room temperature for six hours. Isolate the resulting quaternary salt, 3-methylimidazo[1,5-a]pyridine-1-trimethylammoniummethyl iodide, by filtering and washing with acetone.

EXAMPLE 4

Heat on a steam bath for one hour a mixture containing 2.4 gm (0.007 mol) 3-methylimidazo[1,5-a]pyridine-1-trimethylammoniummethyl iodide and 1.2 gm (0.024 mol) sodium cyanide in 35 ml dimethylformamide. Cool to room temperature, and remove the dimethylformamide in vacuo. Partition the resulting residue between dichloromethane and 10% aqueous sodium hydroxide solution. Extract the aqueous layer with dichloromethane, combine the extracts and dry over anhydrous potassium carbonate. Filter the dried combined extracts and remove the dichloromethane under reduced pressure. Chromatograph the resulting residue on silica gel using ethyl acetate-dichloromethane. Combine the fractions containing the desired product, 1-cyanomethyl-3-methylimidazo[1,5-a]pyridine as determined by IR and NMR, NMR, and remove the solvent under reduced pressure. Triturate the residue in ether to recover the product, m.p. 77°–78°.

In the following formulations the active ingredient is designated by the term "Drug" which is meant to indicate one of the following compounds:

3-cyanomethylimidazo[1,5-a]pyridine;
3-methylimidazo[1,5-a]pyridine; and
1-cyanomethyl-3-methylimidazo[1,5-a]pyridine.

EXAMPLE 5

| No. | Tablet Formulations Ingredient | mg/tab | mg/tab |
|---|---|---|---|
| 1 | Drug | 25.0 | 400.0 |
| 2 | Lactose impalpable powder USP | 114.0 | 241.5 |
| 3 | Corn starch USP | 25.0 | 50.0 |
| 4. | Corn starch as 5% paste in distilled water | 10.0 | 35.0 |
| 5 | Corn starch USP | 25.0 | 50.0 |
| 6 | Magnesium stearate USP | 1.0 | 3.5 |
|   |   | 200.0 | 780.0 |

Method of Manufacture

Mix item nos. 1, 2 and 3 in a suitable blender for 5 to 15 minutes. Pass through a fine screen (#40) if necessary. Reblend for 5 to 10 minutes and granulate with item no. 4. Pass the damp granulated mass through a coarse sieve (#6) using a suitable mill. Dry the damp granules at 40° to 50° C. overnight. Mill the dried granules using no. 20 screen. Add item no. 5 and blend for 5 to 10 minutes. Add item no. 6 and blend further for 3 to 5 minutes. Compress the mixture into tablets of appropriate size and weight using suitable tablet machine.

EXAMPLE 6

| No. | Capsule Formulations Ingredient | mg/tab | mg/tab |
|---|---|---|---|
| 1 | Drug | 25.0 | 400.0 |
| 2 | Lactose, impalpable powder USP | 144.0 | 191.5 |
| 3 | Corn starch USP | 30.0 | 105.0 |
| 4 | Magnesium stearate USP | 1.0 | 3.5 |
|   |   | 200.0 | 700.0 |

Method of Manufacture

Mix item nos. 1, 2 and 3 in a suitable blender for 5 to 10 minutes. Pass through a fine screen (#40) if necessary. Reblend for 5 to 10 minutes, add item no. 4 and mix further for 3 to 50 minutes. Using a suitable machine, encapsulate the mixture into a two piece hard gelatin capsule of appropriate size.

EXAMPLE 7

| Ingredients | Suspension Formulations Formula A (mg/ml) | Formula B (mg/ml) |
|---|---|---|
| Drug | 5.0 | 80.0 |
| Sucrose | 600.0 | 600.0 |
| Benzyl Alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

Method of Manufacture

1. Charge approximately 40% of the final volume of purified water in a stainless steel tank. Heat to boiling. Agitate using an appropriate stirrer. Agitation should continue through procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.
7. This suspension is then q.s. to final volume with purified water at 25° C.

EXAMPLE 8

| Parenteral Formulation | mg/ml |
|---|---|
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

Method for Manufacture

1. Dissolve parabens in a portion (approximately 85% of the final volume) of the water for injection at 65°-70° C.
2. Cool to 25°-35° C. Charge and dissolve sodium bisulfite, disodium edetate and sodium sulfate.
3. Charge and dissolve the Drug.
4. Bring the solution to the final volume by adding water for injection.
5. Filter the solution through 0.22 micron membrane and fill into appropriate containers.
6. Terminally sterilize the units by autoclaving.

EXAMPLE 9

| Parenteral Suspension | mg/ml |
|---|---|
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

Method of Preparation

1. Dissolve parabens in a portion of water for injection at 65°-70° C.
2. Cool to 25°-35° C. Charge and dissolve benzyl alcohol, sodium citrate, disodium edetate, PEG 4000, povidone and sodium carboxymethylcellulose.
3. Filter the solution and sterilize by autoclaving
4. Make a slurry of the sterile Drug and pass it through a colloid mill.
5. Mix it well with solution from Step 3 and pass it through the mill.
6. Bring the suspension to the final volume/weight and fill into sterile containers.

EXAMPLE 10

| A. Formula | Suppositories mg/supp |
|---|---|
| Drug | 5.0 |
| Cocoa butter | 1995.0 |
| | 2.0 g. |

Procedure

1. Melt cocoa butter to about 32°–35° C.
2. Blend Drug into cocoa butter until well dispersed.
3. Pour into teflon-coated mold and congeal in refrigerator. Keep in refrigerator for an appropriate length of time.
4. Remove suppositories from mold.

| B. Formula | mg/supp |
|---|---|
| Drug | 100.0 |
| PEG 1000 | 1824.0 |
| PEG 4000 | 76.0 |
| | 2.0 g. |

Procedure

1. Melt PEG 1000 and PEG 4000 in one container to 50° C.
2. Add Drug to the mixture. Blend until well dispersed.
3. Pour into mold and congeal in refrigerator. Keep in refrigerator for an appropriate length of time.
4. Remove suppositories from mold.

We claim:

1. A compound represented by the formula

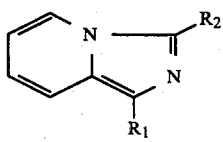

wherein $R_1$ represents hydrogen or cyanomethyl; and $R_2$ represents methyl or cyanomethyl, provided at least one, but not both $R_1$ and $R_2$ are cyanomethyl; and pharmaceutically acceptale salts thereof.

2. A compound of claim 1 wherein $R_1$ is cyanomethyl and $R_2$ is methyl.

3. A compound of claim 1 wherein $R_2$ is cyanomethyl and $R_1$ is hydrogen.

4. A pharmaceutical composition for the treatment of peptic ulcer disease comprising an effective antisecretory and cytoprotective amount of, as the active ingredient, a compound represented by the formula

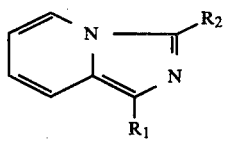

wherein $R_1$ represents hydrogen or cyanomethyl; and $R_2$ represents methyl or cyanomethyl, provided at least one, but not both $R_1$ and $R_2$ are cyanomethyl; and pharmaceutically acceptable salts thereof, together with a pharmaceutically acceptable carrier.

5. The composition of claim 4 wherein the active ingredient is 1-cyanomethyl-3-methylimidazo[1,5-a]pyridine.

6. The composition of claim 4 wherein the active ingredient is 3-cyanomethylimidazo[1,5-a]pyridine.

7. The composition of claims 4, 5, or 6 which is suitable for oral administration.

8. A composition of claims 4, 5, or 6 which is suitable for parenteral administration.

9. A method for treating and promoting healing of peptic ulcer disease in patients in need of such treatment which comprises, administering to such patient an antisecretory and cytoprotective effective amount of a composition of claims 4, 5, or 6.

10. A method for inhibiting the formation of gastrointestinal irritation and ulcers due to administration of drugs which induce such effects, comprising administering to a patient in need of such treatment a therapeutically effective amount of a composition of claims 4, 5 or 6.

* * * * *